US00PP12881P2

(12) United States Plant Patent
Zur et al.

(10) Patent No.: US PP12,881 P2
(45) Date of Patent: Aug. 27, 2002

(54) CURCUMA PLANT NAMED 'THAI BEAUTY'

(75) Inventors: Issachar Ben Zur, Tirat Yehuda (IL); Vitoon Techachareonsukchera, Bangkok (TH)

(73) Assignee: Ben Zur Nurseries Ltd., Tirat Yehuda (IL)

( * ) Notice: Subject to any disclaimer, the term of this patent is extended or adjusted under 35 U.S.C. 154(b) by 0 days.

(21) Appl. No.: 09/569,357

(22) Filed: May 11, 2000

(51) Int. Cl.[7] ..... A01H 5/00
(52) U.S. Cl. ..... Plt./263
(58) Field of Search ..... Plt./263

(56) References Cited

PUBLICATIONS

UPOV ROM GTITM Computer Database 2001/01 GTI JOUVE Retrieval Software, citations for 'Thai Beauty' 2001.*

* cited by examiner

*Primary Examiner*—Bruce R. Campell
*Assistant Examiner*—Wendy C Baker
(74) *Attorney, Agent, or Firm*—C. A. Whealy

(57) ABSTRACT

A distinct cultivar of Curcuma plant named 'Thai Beauty', characterized by its compact growth habit with flowers positioned above the foliage; outwardly arching leaves; freely branching growth habit; early and freely flowering; and purple-colored flower bracts.

1 Drawing Sheet

BACKGROUND OF THE INVENTION

The present Invention relates to a new and distinct cultivar of Curcuma plant, botanically known as *Curcuma alismatifolia,* and hereinafter referred to by the cultivar name Thai Beauty.

The new cultivar is a product of a planned and controlled breeding program conducted by the Inventors in Thailand. The objective of the breeding program is to create compact Curcuma cultivars with unique and attractive flower bract color and shape. The new cultivar originated from a deliberate cross by the Inventors between two unidentified selections of *Curcuma alismatifolia.* The cultivar Thai Beauty was discovered and selected by the Inventors as a plant within the progeny of the stated cross in a controlled environment in Thailand in September, 1997.

Asexual propagation of the new cultivar by tissue culture of meristems and by rhizome divisions in Tirat Yehuda, Israel, has shown that the unique features of this new Curcuma plant are stable and reproduced true to type in successive generations of asexual propagation.

SUMMARY OF THE INVENTION

The new Curcuma has not been observed under all possible environmental conditions. The phenotype may vary somewhat with variations in environment such as temperature, light intensity, fertilizer rate, irrigation amount and frequency, and/or propagation procedures without, however, any variance in genotype.

The following traits have been repeatedly observed and are determined to be the unique characteristics of 'Thai Beauty'. These characteristics in combination distinguish 'Thai Beauty' as a new and distinct cultivar:

1. Plants of the new Curcuma are compact with inflorescences positioned above the foliage.
2. Plants of the new Curcuma are outwardly arching forming a broad inverted triangle.
3. Plants of the new Curcuma are freely branching.

4. Plants of the new Curcuma are early and freely flowering.
5. Plants of the new Curcuma have purple-colored flower bracts.
6. Plants of the new Curcuma produce three to five rhizomes per plant.

Plants of the new Curcuma differ from plants of the parent selections in the following characteristics:

1. Plants of the new Curcuma are much more compact than plants of the parent selections.
2. Leaves of plants of the new Curcuma are outwardly arching whereas leaves of plants of the parent selections are upright and erect. Plants of the new Curcuma are outwardly arching and broad whereas plants of the parent selections are upright and erect.
3. Plants of the new Curcuma have much smaller leaves than plants of the parent selections.
4. Plants of the new Curcuma are more freely branching and more freely flowering than plants of the parent selections.
5. Plants of the new Curcuma have a more rapid growth rate and flower about two weeks earlier than plants of the parent selections.
6. Plants of the new Curcuma have purple-colored flower bracts whereas plants of the parent selections have light pink-colored flower bracts.

Plants of the new Curcuma differ from plants of the cultivar Thai Supreme, disclosed in U.S. Plant patent application Ser. No. 09/569,356, in the following characteristics:

1. Plants of the new Curcuma are shorter than plants of the cultivar Thai Supreme.
2. Plants of the new Curcuma are not as freely flowering as plants of the cultivar Thai Supreme.
3. Plants of the new Curcuma and the cultivar Thai Supreme differ in flower bract coloration.
4. Inflorescences of plants of the new Curcuma are positioned above the foliage whereas inflorescences of plants of the cultivar Thai Supreme are positioned at or just above the foliage.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the actual colors of the new Curcuma. The photograph comprises a top perspective view of a typical plant of 'Thai Beauty'.

DETAILED BOTANICAL DESCRIPTION

The following observations and measurements were recorded on plants grown in Tirat Yehuda, Israel in polyethylene-covered greenhouses and under conditions which closely approximate those used in commercial horticultural practice. During the production of these plants, day temperatures ranged from 25 to 40° C., night temperatures ranged from 20 to 28° C., relative humidity was about 60 to 70%, and light level ranged from 70,000 to 100,000 lux. Plants used for this description were grown as single rhizomes and were about 3.5 months old.

In the following description, color references are made to The Royal Horticultural Society Colour Chart except where general terms of ordinary dictionary significance are used. Numerical measurements represent averages from typical plants of 'Thai Beauty'.

Botanical classification: *Curcuma alismatifolia* cultivar Thai Beauty.

Parentage:

*Female and male parents.*—Unidentified selections of *Curcuma alismatifolia,* not patented.

Propagation:

*Type.*—By tissue culture of meristems or by rhizome divisions.

*From tissue culture, time to initiate roots.*—About 20 days at 25 to 30° C.

*From tissue culture, time to produce a rooted liner.*—About 60 days at 25 to 30° C.

*Rooting characteristics.*—Freely branching; cream-colored.

*Number of rhizomes produced per plant.*—About 3 to 5.

*Rhizome diameter.*—About 1.75 cm.

Plant description:

*Growth habit.*—Compact; upright, but outwardly arching; broad inverted triangle. Very freely branching with about 10 shoots forming from a single rhizome. Appropriate for 12 to 15-cm containers; typically one rhizome per container. Used as a potted plant and also as a garden plant.

*Plant height.*—About 35 cm.

*Plant diameter* (*area of spread*).—About 30 cm.

*Growth rate.*—Rapid growth rate.

*Crop time.*—About 3.5 months are required to produce a finished plant in a 12 to 15-cm container from a single rhizome.

*Leaf arrangement.*—Arrangement: Rosette. Shape: Elliptic. Apex: Narrowly acute. Margin: Entire. Length, mature leaves: About 40 cm. Width, mature leaves: About 27.5 cm. Aspect: Initially upright, then almost horizontal. Texture: Smooth. Color, upper and lower surfaces: 147A to 147B.

Inflorescence description:

*Arrangement.*—About 10 terminal inflorescences develop from a single rhizome. Inflorescences are dense spikes with numerous bracts and bracteole flowers in bract axils. Inflorescences persistent.

*Time of flowering, time to flower.*—In Israel, plants from rhizomes planted in early May will start flowering about 3 months later in early August and will continue to flower until November. Flowering continuous.

*Inflorescence longevity.*—Inflorescences last about 23 days on the plant and about 7 days as a cut flower.

*Rate of inflorescence opening.*—Inflorescences are open about five days after the stage of the bud showing color.

*Fragrance.*—None detected.

*Inflorescence size.*—Length: About 10 cm. Diameter: About 4 cm.

*Flowers.*—Length: About 3 cm. Diameter: About 1.2 cm. Shape: Zygomorphic with one upper petal, two lateral petals and one lower petal. Color: Upper petal: Upper surface, 90A, with white, close to 155D, veins; lower surface, 155D. Lateral and lower petals: Upper surface, 155D with 90A towards the margin; lower surface, 155D.

*Flower bracts.*—Quantity: About 13 per inflorescence. Shape: Almost circular. Apex: Rounded. Margin: Entire. Texture: Thick, leathery, glabrous, waxy. Length: About 5 cm. Width: About 4 cm. Color: Upper surface: Initially green, then becoming purple, 75C; apex, reddish. Lower surface: Initially green, then becoming purple, 80B; apex, greenish brown.

*Peduncle.*—Length: About 12.5 cm. Angle: Upright, erect. Color: 144B.

*Seed.*—Length: About 3.5 mm. Diameter: About 2.5 mm. Shape: Oblong. Color: 168A. Germination percentage; Less than 40 percent.

Disease/insect resistance: Plants of the new Curcuma grown in commercial greenhouses have not shown any unusual susceptibility to pathogens or insects common to Curcuma.

Low temperature tolerance: Plants of the new Curcuma will tolerate temperatures as low as 5° C.

It is claimed:

1. A new and distinct cultivar of Curcuma plant named 'Thai Beauty', as illustrated and described.

* * * * *

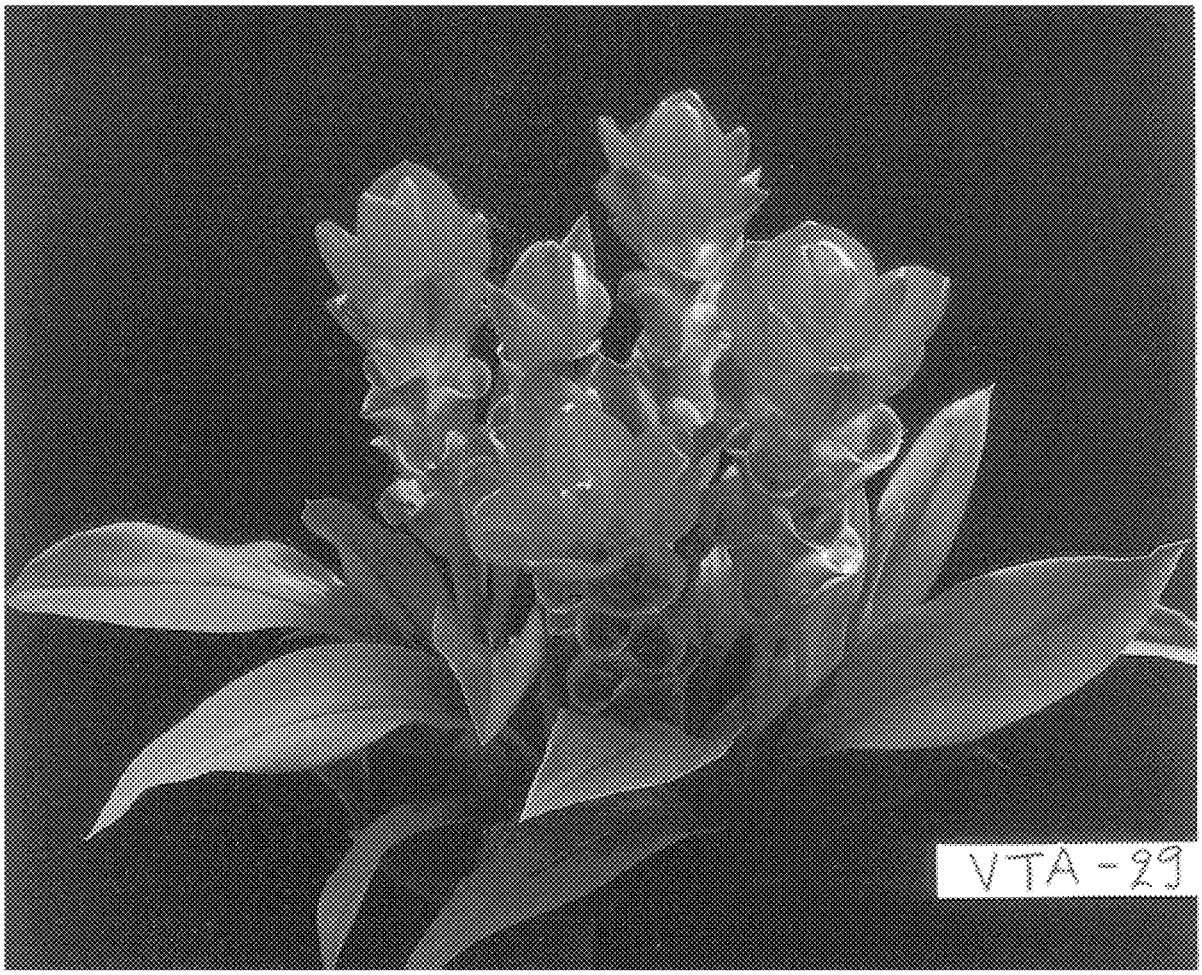
VTA-29